United States Patent [19]

Reinehr

[11] Patent Number: 4,778,928

[45] Date of Patent: Oct. 18, 1988

[54] PROCESS FOR THE PREPARATION OF 4,4'-STILBENEDIALDEHYDES

[75] Inventor: Dieter Reinehr, Kandern, Fed. Rep. of Germany

[73] Assignee: Ciba-Geigy Corporation, Ardsley, N.Y.

[21] Appl. No.: 940,311

[22] Filed: Dec. 10, 1986

[30] Foreign Application Priority Data

Dec. 19, 1985 [CH] Switzerland .................. 5448/85

[51] Int. Cl.$^4$ .................................... C07C 45/00
[52] U.S. Cl. .................................... 568/433; 568/434
[58] Field of Search ............... 568/425, 426, 437, 434, 568/433

[56] References Cited

U.S. PATENT DOCUMENTS

| 4,500,721 | 2/1985 | Yamachika et al. | 568/433 |
| 4,579,975 | 4/1986 | Reinehr et al. | 568/433 |

FOREIGN PATENT DOCUMENTS

| 0104296 | 4/1984 | European Pat. Off. | 568/433 |
| 2732227 | 2/1979 | Fed. Rep. of Germany | 568/433 |

OTHER PUBLICATIONS

Patent Abstracts of Japan, C Section, vol. 1, No. 12, Mar. 22, 1977.

*Primary Examiner*—Werren B. Lone
*Attorney, Agent, or Firm*—Kevin T. Mansfield; Edward M. Roberts

[57] ABSTRACT

The preparation of 4,4'-stilbenedialdehydes by reduction of 4,4'-stilbenedinitriles with an aluminium hydride.

9 Claims, No Drawings

PROCESS FOR THE PREPARATION OF 4,4'-STILBENEDIALDEHYDES

The present invention relates to a novel process for the preparation of 4,4'-stilbenedialdehydes of formula

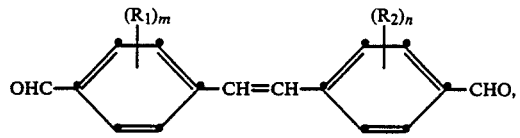

wherein $R_1$ and $R_2$ are each independently of the other substituents that cannot be reduced under the reaction conditions defined below, and m and n are each independently of the other 0, 1 or 2.

The process of the invention comprises reacting the compounds of formula

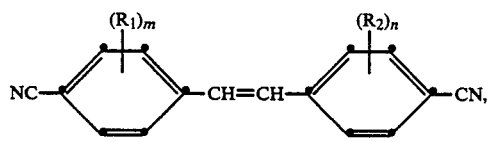

wherein $R_1$, $R_2$, m and n are as defined above, with an aluminium hydride, in an anhydrous, inert, aprotic organic solvent, thereafter subjecting the reaction mixture to an acid hydrolysis, and isolating the compounds of formula (1).

In the compounds of formula (1), $R_1$ and $R_2$ are each independently of the other substituents that are unable to react under the reaction conditions characteristic of the process of the invention. For example, $R_1$ and $R_2$ are alkyl or alkoxy, preferably each of 1 to 4 carbon atoms, aryl or aryloxy such as phenyl or phenoxy, halogen, preferably chlorine or bromine, or dialkylamines containing preferably 1 to 4 carbon atoms in each of the alkyl moieties.

The indices m and n are each independently of the other 0, 1 or 2, and are preferably simultaneously 0.

In the process of the invention, the compounds of formula (2), wherein $R_1$, $R_2$, m and n have the given meanings, are added to an anhydrous, inert, aprotic organic solvent. Examples of suitable solvents are hydrocarbons such as alkanes and cycloalkanes, each of 5 to 10 carbon atoms, e.g. pentane, hexane, heptane, octane, nonane, decane, cyclopentane, cyclohexane, methylcyclohexane, cyclooctane and decalin, as well as aromatic hydrocarbons such as benzene and toluene; and ethers such as diethyl ether or dibutyl ether, dioxane or tetrahydrofuran; as well as mixtures of said solvents.

To this solution or dispersion of the compound of formula (2) is slowly added a solution of an aluminium hydride in preferably the same solvent as the compound of formula (2). Aluminium hydrides which may be suitably employed in the process of this invention are e.g. those of formulae $R_3R_4AlH$, $M[R_3R_4AlH_2]$ or $MAlH_4$, wherein $R_3$ and $R_4$ each independently of the other alkyl of 1 to 4, preferably 2 or 4, carbon atoms, and M is lithium or sodium. Preferred aluminium hydrides are those of formulae $(^iC_4H_9)_2AlH$, $Na[^i(C_4H_9)_2AlH_2]$ and $LiAlH_4$, with particularly good results being obtained with $(^iC_4H_9)_2AlH$.

The addition of the solution of aluminium hydride to the solution of the compound of formula (2) should preferably be made so slowly that the temperature of the reaction mixture does not exceed 50° C. A particularly suitable temperature range for the reduction of this invention is from 15° to 50° C. Owing to the high sensitivity to hydrolysis and air of the alkyl aluminium hydrides, the reduction is carried out in an inert gas, preferably nitrogen, and in an anhydrous solvent that is saturated with an inert gas, preferably nitrogen.

The reaction mixture so obtained is then subjected to acid hydrolysis by slowly adding it to an aqueous solution of an inorganic acid. During this addition, the temperature should be kept in the range from 15° to 50° C., preferably from 30° to 40° C. Suitable inorganic acids are for example hydrochloric acid, sulfuric acid, nitric acid and phosphoric acid, with hydrochloric acid being preferred. The amount of acid employed is preferably such that, after the hydrolysis, the pH of the reaction mixture is low enough to prevent the precipitation of aluminium hydroxide.

The isolation of the compounds of formula (1) can then be effected by methods which are known per se, for example by filtration, after optional removal of the organic solvent by (steam) distillation, or by crystallisation or formation of adducts with sodium bisulfite.

A preferred embodiment of the process of the present invention comprises reacting the compounds of formula (2), wherein m and n are 0, with $(^iC_4H_9)_2AlH$ at 15° to 25° C. in toluene, then subjecting the reaction mixture to hydrolysis in the presence of hydrochloric acid in the temperature range from 30° to 40° C., and isolating the compounds of formula (1).

In the process of the present invention, the molar ratio of the compound of formula (2) to aluminium hydride is 1:1 to 1:5. The greater the excess of aluminium hydride, the lower the reaction temperature during the reduction should be kept so as substantially to prevent secondary reactions, especially the over-reduction of the cyano groups and the reduction of the intermediate double bond of the stilbene derivatives.

Particularly good results are obtained by the process of the invention if the molar ratio is from 1:2 to 1:3 and the reaction temperature during the reduction is in the range from 20° to 25° C.

The invention further relates to the novel intermediates of formula

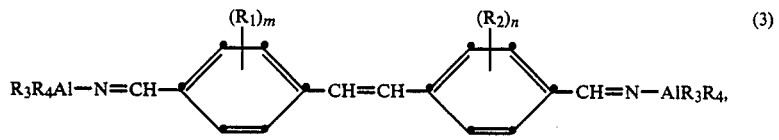

wherein $R_1$, $R_2$, $R_3$, $R_4$, m and n have the given meanings, which are obtainable by the reaction and which, if desired, can be isolated, and to a process for the preparation of said intermediates and to the use thereof and of the compounds of formula (2) for the preparation of 4,4'-stilbenedialdehydes of formula (1).

The preparation of the novel intermediates of formula (3) is carried out e.g. by the above described reduction of the compounds of formula (2) with an aluminium hydride of formula $R_3R_4AlH$ or $M[R_3R_4AlH_2]$, wherein $R_3$, $R_4$ and M have the given meanings, in an anhydrous, inert, aprotic organic solvent. The intermediates are isolated in virtually pure form from the reaction solution. Isolation can be effected in a manner known per se, e.g. by precipitation.

Of these novel intermediates which can be used for the preparation of compounds of formula (1), the compound of formula

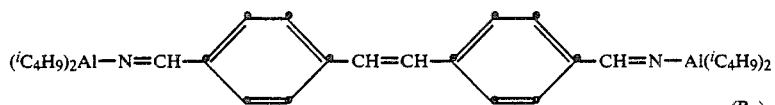

(4)

is especially preferred. It is preferably obtained by reacting the compound of formula (2), wherein m and n are 0, with $(^iC_4H_9)_2AlH$, in toluene and in the temperature range from 15° to 25° C.

The compounds of formula (1) are e.g. useful starting materials for the synthesis of fluorescent whitening agents.

EXAMPLE

In a sulfonating flask, 230 g of 4,4'-stilbenedinitrile are suspended, under a blanket of nitrogen, in 1200 ml of toluene which has been saturated with nitrogen. To this suspension are added 2008 ml of a 20% solution of diisobutyl aluminium hydride in toluene over 1½ hours, whereupon a clear, yellowish, viscous solution forms.

This solution is stirred for 3½ hours at room temperature and then added dropwise over 30 minutes to a mixture of 1 liter of concentrated hydrochloric acid and 2 liters of water. The temperature of the reaction mixture is kept in the range from 30°–40° C. by cooling with an ice bath.

The resultant yellowish suspension is subjected to steam distillation to remove the toluene. The residue in the aqueous bottom is then isolated by filtration, washed with water until neutral, and dried in a vacuum drying cabinet at 80° C., affording 226.2 g (95.7%) of stilbenedialdehyde with a melting point of 168°–170° C.

If desired, further purification can be effected by dissolving the product in toluene, treating the solution once or twice with fuller's earth, and precipitating the product once more by addition of hexane. Yield: 196.7 g (83.3%) of stilbenedialdehyde with a melting point of 169°–171° C.

The compound of formula

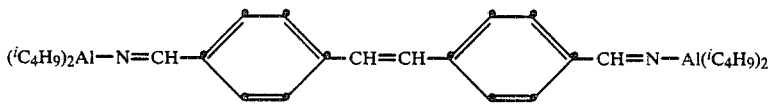

(4)

which can be isolated before the acid hydrolysis, has a melting point above 350° C. The structure of these compounds is confirmed by the NMR spectrum. The following values are obtained by elemental analysis:

|   | found | theory |
|---|-------|--------|
| C | 70.5% | 74.7%  |
| H | 9.0%  | 9.4%   |

-continued

|    | found  | theory |
|----|--------|--------|
| N  | 5.1%   | 5.4%   |
| Al | 11.0%  | 10.5%  |

What is claimed is:

1. A process for the preparation of a 4,4'-stilbenedialdehyde of formula

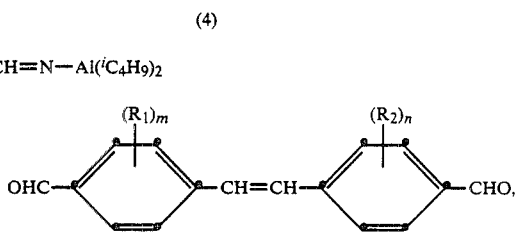

(1)

wherein $R_1$ and $R_2$ are each independently of the other alkyl or alkoxy of 1 to 4 carbon atoms, phenyl, phenoxy, chlorine, bromine or $C_1$-$C_4$-dialkylamino, and m and n are each independently of the other 0, 1 or 2, which process comprises reacting a compound of formula

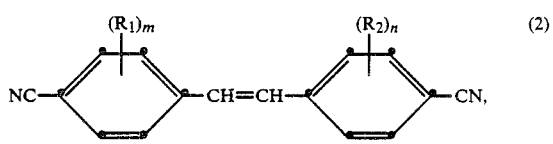

(2)

wherein $R_1$, $R_2$, m and n have the given meanings, with an aluminum hydride, in an anhydrous, inert, aprotic organic solvent, thereafter subjecting the reaction mixture to acid hydrolysis, and isolating the compound of formula (1).

2. A process according to claim 1, wherein the solvent is a hydrocarbon, an ether or a mixture thereof.

3. A process according to claim 2, wherein the solvent is an alkane or cycloalkane, each of 5 to 10 carbon atoms, an aromatic hydrocarbon, dioxane, tetrahydrofuran, dibutyl ether, diethyl ether, or a mixture of said solvents.

4. A process according to claim 1, wherein the aluminium hydride is a compound of formula $R_3R_4AlH$, $M[R_3R_4AlH_2]$ or $MAlH_4$, wherein $R_3$ and $R_4$ are each independently of the other alkyl of 1 to 4 carbon atoms, and M is lithium or sodium.

5. A process according to claim 4, wherein the aluminium hydride is $(^iC_4H_9)_2AlH$, $Na[^i(C_4H_9)_2AlH_2]$ or $LiAlH_4$.

6. A process according to claim 1, wherein the acid hydrolysis is carried out in the presence of hydrochloric acid, sulfuric acid, nitric acid or phosphoric acid.

7. A process according to claim 1, wherein the reduction and the acid hydrolysis are carried out in the temperature range from 15° to 50° C.

8. A process according to claim 1, which comprises reacting the compound of formula (2), wherein m and n are 0, with $(^iC_4H_9)_2AlH$ at 15° to 25° C. in toluene, then subjecting the reaction mixture to hydrolysis in the presence of hydrochloric acid in the temperature range from 30° to 40° C., and isolating the compound of formula (1).

9. A process according to claim 8, wherein the molar ratio of the compound of formula (2) to aluminium hydride is 1:1 to 1:5.

* * * * *